United States Patent [19]

Hayashi et al.

[11] Patent Number: 4,754,060

[45] Date of Patent: Jun. 28, 1988

[54] PROCESS FOR PRODUCING NAPHTHALENEDICARBOXYLIC ACID TOGETHER WITH TRIMELLITIC ACID

[75] Inventors: Shoichiro Hayashi; Toshiharu Matsuda; Atsushi Sasakawa, all of Iwaki, Japan

[73] Assignee: Kureha Kagaku Kogyo Kabushiki Kaisha, Tokyo, Japan

[21] Appl. No.: 22,962

[22] Filed: Mar. 6, 1987

[30] Foreign Application Priority Data

Mar. 14, 1986 [JP] Japan ................................ 61-56356

[51] Int. Cl.$^4$ ............................................ C07C 51/265
[52] U.S. Cl. ...................................... 562/414; 562/416
[58] Field of Search ........................ 562/414, 416, 486

[56] References Cited

U.S. PATENT DOCUMENTS 3,870,754  3/1975  Yamashita et al. ................. 562/416
4,709,088  11/1987  Hirose et al. .................. 562/416 X

FOREIGN PATENT DOCUMENTS 48-27318  8/1973  Japan .
56-3858   1/1981  Japan .
60-89445  5/1985  Japan .
60-89446  5/1985  Japan .

Primary Examiner—Donald B. Moyer
Assistant Examiner—Patricia M. Scott
Attorney, Agent, or Firm—Nixon & Vanderhye

[57] ABSTRACT

Disclosed herein is a process for producing 2,6-naphthalenedicarboxylic acid together with trimellitic acid comprising oxidizing 2,6-diisopropylnaphthalene with molecular oxygen in the presence of a catalyst comprising a heavy metal(s) and bromine.

5 Claims, No Drawings

PROCESS FOR PRODUCING NAPHTHALENEDICARBOXYLIC ACID TOGETHER WITH TRIMELLITIC ACID

BACKGROUND OF THE INVENTION

The present invention relates to a process for producing 2,6-naphthalenedicarboxylic acid together with trimellitic acid by oxidation of 2,6-diisopropylnaphthalene (hereinafter referred to as "2,6-DIPN").

2,6-naphthalenedicarboxylic acid is useful as a starting material for polyethylene naphthalate, polyester, polyamide, etc. which are useful as a material for films and synthetic fibers having excellent heat resistance and mechanical properties, while anhydrous trimellitic acid is useful as a starting material for heat-resistant plasticizing ester, polyimide resins, curing agents for epoxy resin, coating materials and stabilizers.

Conventionally, trimellitic acid was synthesized by oxidation of pseudocumene with chromic acid or oxidation of rosin with nitric acid, but at present it is more industrially produced by air-oxidation of pseudocumene.

As a process for producing 2,6-naphthalenedicarboxylic acid (hereinunder referred to as "2,6-NDCA"), a method of oxidizing 2,6-dialkylnaphthalene such as 2,6-dimethylnaphthalene and 2,6-diisopropylnaphthalene in a solvent of acetic acid with molecular oxygen in the presence of a catalyst comprising cobalt and/or manganese, and bromine has been proposed (e.g., Japanese Patent Publication No. 48-27318 (1973), Japanese Patent Application Laying-Open (KOKAI) No. 60-89445 (1985) and Japanese Patent Application Laying-Open (KOKAI) No. 60-89446 (1985)).

According to such a method, since a large amount of bromine is used as compared with that of a heavy metal(s) in a mixed catalyst in order to obtain 2,6-NDCA with high yield, not only the alkyl group of 2,6-dialkylnaphthalene is oxidized but also the naphthalene ring is brominated, thereby producing various kinds of bromonaphthalenedicarboxylic acids as by-products as well as 2,6-NDCA. Since the physical and chemical nature of these bromonaphthalenedicarboxylic acids resemble those of 2,6-NDCA, it is very difficult to separate those bromonaphthalenedicarboxylic acids from 2,6-NDCA for purification. Therefore, removal of by-product bromides from crude 2,6-NDCA is the most important in producing 2,6-NDCA, as described in detail, for example, in Japanese Patent Publication No. 56-3858 (1981). Resins such as polyethylene naphthalate obtained from 2,6-NDCA contaminated by remaining bromides have a low softening point, and it is difficult to produce a film, fiber, etc. having high heat resistance and good mechanical properties out of such a contaminated 2,6-NDCA. In the above-described methods for producing 2,6-NDCA, aldehydes and colored substances having unknown structures are undesirably produced as by-products as well as bromonaphthalenedicarboxylic acids. These by-products are also difficult to separate and remove from 2,6-NDCA. Therefore, a conventional process for producing 2,6-NDCA requires many steps for separation and purification of 2,6-NDCA.

For example, in the method for producing 2,6-NDCA disclosed in Japanese Patent Publication No. 56-3858 (1981), 2,6-NDCA is obtained by oxidizing 2,6-dimethylnaphthalene with molecular oxygen in the presence of a catalyst comprising bromine, cobalt and manganese. Since a large amount of bromine is used as compared with that of cobalt and manganese (the atomic ratio of bromine to cobalt and manganese is 1.7), 1,000 to 2,000 ppm of bromine is contained in the crude 2,6-NDCA which is separated from the reaction mixture and 10 to 40 ppm bromine is still contained even after purification.

As described above, in the conventional processes for producing 2,6-NDCA using a large amount of bromine, a large amount of bromonaphthalenedicarboxylic acids, aldehydes, colored substances having unknown structure are produced as by-products. Therefore, many complicated steps of purification are required for producing high-purity 2,6-NDCA to remove these by-products from the crude 2,6-NDCA, so that the conventional processes are unsatisfactory. Particularly, removal of bromides which have a fatal influence on resin products obtained from 2,6-NDCA is difficult. Thus, it is extremely difficult to produce 2,6-NDCA of a satisfactorily high purity by a conventional process.

As a result of researches by the present inventors on a process for producing high-purity 2,6-NDCA, in particular, 2,6-NDCA substantially free from bromine, it has been found that if the atomic ratio of bromine to cobalt and/or manganese in the catalyst is reduced much more than in a conventional process, in a process for producing 2,6-NDCA by oxidizing 2,6-DIPN with molecular oxygen in the presence of a catalyst comprising cobalt, manganese or a mixture thereof and bromine, production of by-products, in particular, production of bromides such as a bromonaphthalenedicarboxylic acid is suppressed, thereby producing 2,6-NDCA with high purity together with high-purity trimellitic acid and, in addition, the recovery and regeneration of a catalyst of a heavy metal(s) is facilitated. The present invention has been achieved on the basis of this finding.

SUMMARY OF THE INVENTION

In an aspect of the present invention, there is provided a process for producing 2,6-naphthalenedicarboxylic acid together with trimellitic acid comprising the steps of:

oxidizing 2,6-diisopropylnaphthalene in a solvent of a lower aliphatic monocarboxylic acid containing not more than 30 wt % water with molecular oxygen in the presence of a catalyst comprising cobalt, manganese or a mixture thereof and bromine of not less than 0.0001 and less than 0.01 in an atomic ratio to the heavy metals;

cooling the reaction mixture and separating 2,6-naphthalenedicarboxylic acid and the heavy metal salt(s) of trimellitic acid as a solid;

adding the separated mixture to an aqueous solution of a mineral acid so that the pH of the solution is not higher than 3 to dissolve the heavy metal salts of trimellitic acid, and filtering out insoluble 2,6-naphthalenedicarboxylic acid;

concentrating the filtrate while maintaining the pH of the filtrate at not higher than 3, cooling the filtrate, and filtering out trimellitic acid; and adding an alkali carbonate, an alkali dicarbonate, or the mixture thereof to the filtrate to recover the heavy metal(s) as an alkali carbonate(s), a basic alkali carbonate(s) or a mixture thereof.

DETAILED DESCRIPTION OF THE INVENTION

A process for producing 2,6-naphthalenedicarboxylic acid together with trimellitic acid according to the present invention comprises the steps of oxidizing 2,6-DIPN in a solvent of a lower aliphatic monocarboxylic acid containing not more than 30 wt % water with molecular oxygen in the presence of a catalyst comprising cobalt, manganese or a mixture thereof and bromine of not less than 0.0001 and less than 0.01 in an atomic ratio to the heavy metal or metals;

cooling the reaction mixture and separating 2,6-NDCA and the heavy metal salt(s) of trimellitic acid as a solid;

adding the separated 2,6-NDCA and heavy metal salt(s) of trimellitic acid to an aqueous solution of a mineral acid so that the pH of the solution is not higher than 3 to dissolve only the heavy metal salt(s) of trimellitic acid, and separating 2,6-NDCA which is insoluble in the aqueous solution of mineral acid by filtration;

concentrating the filtrate while maintaining the pH of the filtrate at not higher than 3, cooling the filtrate and separating trimellitic acid by filtration; and adding an alkali carbonate, an alkali hydrogen carbonate, or the mixture thereof into the filtrate to recover the heavy metal(s) as a precipitate of an alkali carbonate(s), a basic alkali carbonate(s) or a mixture thereof.

The solvent used in the present invention is a lower aliphatic monocarboxylic acid containing not more than 30 wt %, preferably not more than 15 wt % water. If the water content is over 30 wt %, not only is the rate of oxidation greatly reduced, but also the heavy metal salts of trimellitic acid are dissolved in the solvent, thereby reducing the recovery of the heavy metal salt(s) of trimellitic acid in separating as insoluble(s). In addition, the purity of trimellitic acid is disadvantageously lowered. As the lower aliphatic monocarboxylic acid, for example, formic acid, acetic acid, propionic acid and butyric acid, which have not more than 4 carbon atoms, may be used. Among these, acetic acid is the most preferable.

The cobalt and manganese components of the catalyst used in the present invention are exemplified by inorganic compounds such as oxides, hydroxides, carbonates and halides of cobalt or manganese, and cobalt salts or manganese salts of fatty acids such as formic acid, acetic acid and propionic acid and organic acids such as naphthenic acid and aromatic carboxylic acid. Among these, salts of fatty acids and, in particular, cobaltous acetate and manganese acetate are preferable.

As the bromine component of the catalyst used in the present invention, any of bromine element, inorganic and organic compounds of bromine is usable so long as it is dissolved in a solvent for oxidation reaction and generates bromide ions. For example, molecular bromine, inorganic bromine compounds such as hydrogen bromide and inorganic bromides, alkyl bromides such as methyl bromide and ethyl bromide, and brominated fatty acids such as bromoacetic acid may be used. Among these, hydrogen bromide, sodium bromide, potassium bromide, ammonium bromide, cobaltous bromide, manganese bromide, etc. are preferable.

As the molecular oxygen used in oxidation, oxygen gas or a mixed gas of oxygen and inert gas is usable, but compressed air is industrially preferable. The higher the partial pressure of oxygen in the reaction system is, the more quickly oxidation proceeds, but in practical use, the partial pressure of oxygen of not less than 0.1 kg/cm$^2$ (absolute pressure; the same shall apply hereinafter), preferably 0.2 to 8 kg/cm$^2$ is sufficient, and little industrial merit is found in adopting a partial pressure exceeding 8 kg/cm$^2$. When a mixed gas is used, the total pressure is not specifically limited, but a pressure of 7 to 30 kg/cm$^2$ is sufficient for practical use.

The oxidation temperature is 140° to 210° C., preferably 160° to 200° C. If the temperature is lower than 140° C., the reaction rate is greatly lowered, while an oxidation temperature exceeding 200° C. causes disadvantageous increase of the loss of the solvent by burning.

The amount of cobalt, manganese or a mixture thereof used in the present invention is preferably 0.005 to 0.2 mol, more preferably 0.01 to 0.12 mol, to 100 g of the solvent used for reaction. If a large amount of cobalt and manganese or a mixture thereof is used beyond 0.2 mol to 100 g of the solvent, the amount of by products is increased. On the other hand, if the amount thereof is less than 0.005 mol to 100 g of the solvent, the yields of 2,6-NDCA and trimellitic acid are disadvantageously reduced. Cobalt and manganese may be used singly or as a mixture thereof, but a mixture is preferable, because it exhibits a higher activity. In this case, the mixing ratio of cobalt and manganese is not specially restricted because it depends on other reaction conditions such as the reaction temperature, the amount of bromine and the partial pressure of oxygen, but the atomic ratio of cobalt to manganese is preferably 5:95 to 70:30.

The amount of bromine is not less than 0.0001 and less than 0.01, preferably 0.0005 to 0.008 in an atomic ratio to the total amount of cobalt and manganese.

Japanese Patent Application Laying-Open (KOKAI) No. 60-89445 (1985) discloses that although the amount of bromine depends upon not only the concentration of a heavy metal(s) but also the reaction conditions such as the reaction temperature, the concentration of a starting material and the amount of a solvent, but it is preferably 0.01 to 2 in an atomic ratio to the amount of the heavy metal. However, according to the findings of the present inventors, use of bromine of not less than 0.01 in an atomic ratio to a heavy metal produced a considerable amount of bromonaphthalenedicarboxylic acid as a by-product which was difficult to remove, and it was extremely difficult to obtain high-purity 2,6-NDCA and trimellitic acid. Even if bromine of less than 0.01 in an atomic ratio to cobalt and manganese is used, a bromide is inevitably produced as a by-product, but the amount of by-product is very small, and it is easy to reduce the bromine content in 2,6-NDCA and trimellitic acid to not more than 1 ppm by the purification method described, for example, in Japanese Patent Publication No. 56-3858 (1981). Since use of an extremely small amount of bromine reduces the oxidation rate economically disadvantageously, it is preferable to use bromine of not less than 0.0001 in an atomic ratio to cobalt and manganese.

Incidentally, when the catalyst used in the present invention which contains a trace amount of bromine is used in oxidation of aromatic hydrocarbon having a methyl group such as p-xylene and 2,6-dimethylnaphthalene, the activity of the catalyst is too low for practical use. In contrast, when the catalyst is used in oxidation of 2,6-DIPN, since the hydrogen on the tertiary carbon of the isopropyl group is more active than the hydrogen of the methyl group, oxidation proceeds in the presence of such a catalyst in which the bromine content is extremely small and, in addition, it is possible to suppress the production of a by-product(s) such as bromonaphthalenedicarboxylic acid, as described above.

In the present invention, the amount of the starting material 2,6-DIPN supplied into the reaction system is preferably not more than 20 parts by weight to 100 parts by weight of the reaction solvent. If more than 20 parts by weight of 2,6-DIPN to 100 parts by weight of the solvent exists in the reaction system, the concentration of unstable oxidation intermediates increases, while the amount of molecular oxygen dissolved in the solvent relatively decreases. As a result, the amount of by-products such as aldehydes, oxidative-polymerization products and colored substances increase, thereby disadvantageously reducing the yields of 2,6-NDCA and trimellitic acid. The amount of 2,6-DIPN in the reaction system is preferably not more than 0.4, more preferably 0.05 to 0.3 in a mol ratio to the total amount of cobalt and manganese in the oxidation catalyst in order to suppress the side reaction.

When 2,6-DIPN is oxidized under the above-described conditions, 2,6-NDCA and trimellitic acid can be produced advantageously.

2,6-NDCA, which has a very small solubility in the reaction solvent, separates out with the proceeding of the reaction and about 98% of the produced 2,6-NDCA separates out as a free acid by the end of the reaction. On the other hand, trimellitic acid is highly soluble in the reaction system, but when substantially all the 2,6-DIPN in the reaction system is consumed and the concentration of the oxidation intermediate, 6-isopropyl-2-naphthoic acid is reduced down to not more than 1%, trimellitic acid forms the insoluble 1:1 salt(s) with cobalt, manganese, or a mixture thereof, and about 97% of the produced trimellitic acid separates out.

After the end of the reaction, the reaction mixture is cooled to 90° C. or lower and filtered to obtain a mixture of 2,6-NDCA and the heavy metal salt(s) of trimellitic acid. It is possible to use the filtrate repeatedly as the solvent for reaction after adjusting the water content thereof, if necessary.

When the mixture of 2,6-NDCA and the heavy metal salt(s) of trimellitic acid obtained is added to an aqueous solution of a mineral acid, such as hydrochloric acid, nitric acid or sulfuric acid and the solution is adjusted to pH of not higher than 3, preferably 1 to 2, the heavy metal salt(s) of trimellitic acid alone are dissolved. When the insoluble 2,6-NDCA is filtered out and washed with water, crude 2,6-NDCA having a purity of about 98% and containing not more than 100 ppm bromine is substantially quantatively recovered.

The filtrate is next concentrated while maintaining the pH thereof at not higher than 3, preferably 1 to 2 and cooled to separate trimellitic acid, which is washed with water to recover trimellitic acid having a purity of 98% and containing not more than 50 ppm of bromine. Preferably the steps of concentration and separation are repeated several times in order to facilitate the filtration and prevent trimellitic acid being accompanied by the heavy metals. If the pH of the filtrate is higher than 3, trimellitic acid is contaminated by the heavy metals and it is difficult to obtain high-purity trimellitic acid, so the adjustment of pH is important.

The filtrate from which trimellitic acid has been separated contains cobalt and manganese dissolved therein, and it is economically important to recover the heavy metals. In order to recover the heavy metals, an alkali carbonate, an alkali hydrogen carbonate or a mixture thereof is added to the filtrate so that the pH of the solution is not less than 7, preferably 9 to 10. Then, cobalt and/or manganese are precipitated as a water-insoluble carbonate(s) and/or a basic carbonate(s), thereby facilitating recovery of the heavy metal(s). In this case, it is important to use the above-described alkali carbonate and/or alkali hydrogen carbonate to adjust the pH. For example, if an alkali hydroxide is used, the heavy metal salt(s) is precipitated in the form of such a fine precipitate(s) that it is difficult to filter it out and to remove other alkali metal salts which have adhered to the precipitated heavy metal salt(s) by washing with water. If the heavy metal(s) containing such alkali metal salts as impurities are used again as an oxidation catalyst(s), the alkali metals are stored in the reaction system and exercise a deleterious effect on oxidation.

According to the present invention, it is easy to control the ratio of the amounts of 2,6-NDCA and trimellitic acid to be produced in the range in which the yield of trimellitic acid does not exceed 60% by controlling, for example, the amount of the catalyst used in oxidation, namely the amount of cobalt and/or manganese and bromine. For example, when 0.017 mol of 2,6-DIPN is oxidized in 100 g of acetic acid with compressed air of 20 kg/cm$^2$ at 180° C., if the catalyst is used in an amount of 0.1 mol as a heavy metal(s) to 100 g of acetic acid, the yield of 2,6-NDCA is 80 to 85%, and the yield of trimellitic acid is 10 to 15%. On the other hand, if the catalyst is used in an amount of 0.01 mol as a heavy metal to 100 g of acetic acid, the yield of 2,6-NDCA is 43 to 55%, and the yield of trimellitic acid is 40 to 52%. In this way, it is possible to control the ratio of the amounts of 2,6-NDCA and trimellitic acid to be produced in accordance with the purpose of production.

In this case, it is also important that the atomic ratio of the amount of bromine to the total amount of cobalt and manganese is not less than 0.0001 and less than 0.01.

As described above, a process for producing 2,6-NDCA together with trimellitic acid according to the present invention is advantageous in that since the production of by-products is very small, 2,6-NDCA is produced with high purity, in that many purification steps which are required in a conventional process for producing 2,6-NDCA are dispensed with, and in that trimellitic acid is also obtained with high purity. Thus, this process is capable of industrially producing 2,6-NDCA together with trimellitic acid.

The present invention will be explained further in detail while referring to the following non-limitative examples.

The purity of 2,6-NDCA and trimellitic acid was measured by a high performance liquid chromatography (A) and the bromine content was measured by X-ray fluorometry (B).

(A) Model 510 type HPLC manufactured by Waters Co.
  Column: coupled column of Lichrosorb (RP-8, 5 μm, manufactured by Merck & Co.) and radial pack cartridge C-8 (manufactured by Waters Co.)
  Mobile phase: water of pH 3/acetonitrile=45/55 (by volume)
  Flow rate: 0.6 cc/min.
  Internal standard: 2-naphthoic acid
  Detection Wavelength: 260 nm (B) RIGAKUDENKI X-ray fluorometer (3080E 2 type)
X-ray tube: rhodium, 50 kV, 50 mA
Detector: PC detector
Crystals: germanium
Detection limit: 3 ppm
10 g of a sample as a tablet of 30 mm in diameter was subject to the measurement.

EXAMPLE 1

2070 g of glacial acetic acid, 130 g of cobalt acetate tetrahydrate, 400 g of manganese acetate tetrahydrate, 1.2 g of ammonium bromide and 75 g of 2,6-diisopropylnaphthalene were put into a 5-l autoclave of stainless steel lined with titanium and equipped with a reflux condenser, a gas inlet tube, a temperature measuring tube and a stirrer. The mixture was heated at 180° to 190° C. and vigorously stirred for 5 hours while blowing compressed air at a rate of 300 an hour under the pressure of 20 kg/cm$^2$. After the reaction, the reaction mixture was cooled to 80° C., and the precipitate was filtered out, thoroughly washed with hot acetic acid and was dried to obtain 77 g of crude crystals (A). 6% dilute sulfuric acid was added to the crude crystals (A) under stirring to adjust the pH of the mixture to 1.5. After stirring the mixture at 80° to 90° C. for 60 minutes, the mixture was filtered while hot, to obtain pale yellow powder. This powder was thoroughly washed with water and dried to obtain 64.2 g of powder. As a result of the purity test and the bromine determination of the powder obtained, the purity proved to be 97.3% and the bromine content was 75 ppm. No trimellitic acid was contained in the powder. The yield of 2,6-NDCA based on the raw material was 81.8%.

The filtrate and the washing were combined and adjusted to pH 1.5 with 6% dilute sulfuric acid and was thereafter concentrated to about 50 g. The concentrate was cooled to 25° C. and precipitated pale yellow crystals of crude trimellitic acid were filtered out and washed to obtain crude crystals. After the filtrate and the washing were adjusted again to pH 1.5, a similar process was repeated to obtain pale yellow crude crystals again. The total amount of the crude crystals after drying was 7.9 g. As a result of the purity test and the bromine determination of the crude crystals, the purity proved to be 98.9% and the bromine content was 45 ppm. The yield of trimellitic acid based on the raw material was 10.5%.

When an aqueous solution of 25% sodium carbonate was added to the filtrate and the washing after the separation and the recovery of trimellitic acid while stirring the mixture at 30° C. to adjust the pH to 9.5, precipitate was generated. The precipitate was filtered out and dried to obtain 10.5 g of basic carbonates of cobalt and manganese. Analysis by atomic absorption spectroscopy proved that the recoveries of cobalt and manganese were 98.6% and 99.0%, respectively, based on the cobalt and manganese contained in the crude crystals (A). When the recovered basic carbonates of cobalt and manganese were added to 250 g of acetic acid and the mixture was stirred at 80° to 90° C. for 4 hours, the basic carbonates were completely dissolved in the acetic acid while generating carbon dioxide gas. The filtrate and the washing after the above-described oxidation were added to the acetic acid solution and the mixture was concentrated to 2.62 kg. Oxidation was carried out by adding 75 g of 2,6-diisopropylnaphthalene to the concentrate under the same conditions as the above. The oxidation proceeded normally and trimellitic acid and 2,6-NDCA were produced with similar yields.

EXAMPLE 2

2070 g of glacial acetic acid, 13 g of cobaltous acetate tetrahydrate, 40 g of manganese acetate tetrahydrate, 0.12 g of ammonium bromide and 75 g of 2,6-diisopropylnaphthalene were put into the same autoclave as used in Example 1 and the mixture was heated at 180° to 190° C. and vigorously stirred for 5 hours while blowing compressed air at a rate of 300 l an hour under the pressure of 20 kg/cm$^2$. The reaction mixture was subjected to the same treatment to that of Example 1 to obtain 82.5 g of a mixture (B) of cobalt and manganese salts of trimellitic acid and 2,6-NDCA. The mixture (B) was further subjected to the same treatment as in Example 1 to obtain 39.1 g of 2,6-NDCA and 32.5 g of trimellitic acid. The yields of 2,6-NDCA and trimellitic acid based on the raw material were 50.0% and 43.2%, respectively. The purity of 2,6-NDCA was 97.6% and the bromine content was 63 ppm. The purity of trimellitic acid was 98.1% and the bromine content was 35 ppm.

When an aqueous solution of 25% sodium carbonate was added to the filtrate after the separation and recovery of trimellitic acid and the mixture was subjected to the same treatment as in Example 1, 98.5% and 99.2% of the cobalt and the manganese, respectively, contained in the mixture (B) were recovered.

EXAMPLE 3

2.8 kg of glacial acetic acid, 180 g of cobaltous acetate tetrahydrate, 530 g of manganese acetate tetrahydrate and 2 g of ammonium bromide were put into a 5-l autoclave of stainless steel lined with titanium and equipped with a reflux condenser, a gas inlet tube, a gas outlet tube, an overflow slurry outlet connected to a stainless steel vessel of inner volume of 30 l, and a stirrer. Compressed air was blown into the mixture at the rate of 600 l an hour under a pressure of 20 kg/cm$^2$ while stirring the mixture at 170° to 190° C. Simultaneously, a solution of 1.67 kg of 2,6-DIPN, 16.7 kg of glacial acetic acid, 1.06 kg of cobaltous acetate tetrahydrate, 3.15 kg of manganese acetate tetrahydrate and 11.7 g of ammonium bromide was continuously supplied to the mixture at the rate of 994 g an hour. After 16-hour reaction, the reaction mixture remaining in the autoclave and overflown into the vessel were cooled to 90° C. The precipitate was filtered out, and after being thoroughly washed with hot acetic acid the precipitate was dried to obtain 1210 g of a mixture (C) of 2,6-NDCA and the cobalt and manganese salts of trimellitic acid.

About 3 kg of water and 10% dilute hydrochloric acid was added to the mixture(s) under stirring to adjust the pH of the mixture to 1.5. After the mixture was stirred at 70° to 80° C. for one hour, pale yellow precipitate was filtered out while hot, thoroughly washed with water and dried to obtain 1.03 kg of crude 2,6-NDCA. The purity of the crude 2,6-NDCA was 97.8% and the bromine content was 97 ppm. The content of trimellitic acid therein was 0.04%, and the yield of 2,6-NDCA based on the raw material was 84.3%.

The filtrate and the washing after the separation of 2,6-NDCA were adjusted to pH 1.5 with hydrochloric acid and was thereafter concentrated to about 840 g. The concentrate was cooled to 25° C. to precipitate pale yellow crystals. The precipitate was filtered out and washed to obtain trimellitic acid. The filtrate and the washing were subjected to the same treatment as in Example 1 to obtain trimellitic acid again. The total amount of trimellitic acid after drying was 134 g. The purity was 98.6% and the bromine content was 44 ppm. The yield of trimellitic acid based on the raw material was 11.4%.

An aqueous solution of 10% sodium carbonate and 10% sodium dicarbonate was added to the filtrate and the washing after the separation and the recovery of trimellitic acid to adjust the pH to 9.5, and cobalt and manganese were recovered in the same manner as in Example 1. The recoveries of cobalt and manganese were 98.1% and 98.8%, respectively, based on the cobalt and manganese contained in the mixture (C).

The crude 2,6-NDCA was purified in accordance with Example 4 disclosed in Japanese Patent Publication No. 56-3858 (1981). That is, 100 g of 2,6-NDCA was dissolved in 800 g of an aqueous solution of 5% NaOH under heating. 10 g of active carbon powder was added thereto and after being stirred at 20° C. for 30 minutes, the mixture was filtered. 6N dilute hydrochloric acid was added to the filtrate under stirring, while maintaining the filtrate at 60° C. When the pH of the filtrate was lowered to 7.0, the filtrate was cooled to 20° C. and was stirred for 30 minutes, thereby separating the crystals of monosodium salt of 2,6-NDCA. The crystals were filtered out and dissolved in 2 kg of water. When 6N dilute hydrochloric acid was added thereto under stirring at 90° C. to adjust the pH to 2, 2,6-NDCA was separated. The separated 2,6-NDCA was filtered out while hot, washed with water and dried to obtain 81.4 g of purified 2,6-NDCA. The purity was 99.1% and no bromine was detected (detection limit: 3 ppm).

What is claimed is:

1. A process for producing 2,6-naphthalenedicarboxylic acid together with trimellitic acid comprising the steps of:

oxidizing 2,6-diisopropylnaphthalene at a temperature of 140°–210° C. in a solvent of a lower aliphatic monocarboxylic acid containing not more than 30 wt % water with molecular oxygen in the presence of an oxidation catalyst comprising cobalt, manganese or a mixture thereof and bromine of not less than 0.0001 and less than 0.01 in an atomic ratio to the heavy metal(s);

cooling the reaction mixture and separating 2,6-naphthalenedicarboxylic acid and the heavy metal salt(s) of trimellitic acid as a solid;

adding the separated mixture to an aqueous solution of a mineral acid so that the pH of said solution is not higher than 3 to dissolve said heavy metal salt(s) of trimellitic acid, and filtering out insoluble 2,6-naphthalenedicarboxylic acid;

concentrating the filtrate while maintaining the pH of said filtrate at not higher than 3, cooling said filtrate and filtering out trimellitic acid; and adding an alkali carbonate, an alkali hydrogen carbonate or a mixture thereof into the filtrate to recover said heavy metal(s) as the precipitate of an alkali carbonate(s), a basic alkali carbonate(s) or a mixture thereof.

2. A process according to claim 1, wherein said lower aliphatic monocarboxylic acid is one selected from the group consisting of formic acid, acetic acid, propionic acid and butyric acid.

3. A process according to claim 1, wherein said cobalt, manganese or mixture thereof is used in an amount of 0.005 to 0.2 mol to 100 g of said solvent.

4. A process according to claim 1, wherein the ratio of cobalt to manganese in said mixture of cobalt and manganese is 5:95 to 70:30 in an atomic ratio.

5. A process according to claim 1, wherein said oxidation catalyst comprises the cobalt salt of a fatty acid, the manganese salt of a fatty acid or a mixture thereof and an inorganic bromide.

* * * * *